United States Patent
Kondou et al.

(10) Patent No.: US 10,849,834 B2
(45) Date of Patent: Dec. 1, 2020

(54) COSMETIC GEL SHEET AND MANUFACTURING METHOD THEREOF

(71) Applicant: COSMED PHARMACEUTICAL CO., LTD., Kyoto (JP)

(72) Inventors: Naoko Kondou, Kyoto (JP); Ying-shu Quan, Kyoto (JP); Fumio Kamiyama, Kyoto (JP)

(73) Assignee: COSMED PHARMACEUTICAL CO., LTD., Kyoto (JP)

( * ) Notice: Subject to any disclaimer, the term of this patent is extended or adjusted under 35 U.S.C. 154(b) by 0 days.

(21) Appl. No.: 15/119,321

(22) PCT Filed: Feb. 12, 2015

(86) PCT No.: PCT/JP2015/053761
§ 371 (c)(1),
(2) Date: Aug. 16, 2016

(87) PCT Pub. No.: WO2015/122433
PCT Pub. Date: Aug. 20, 2015

(65) Prior Publication Data
US 2017/0007509 A1 Jan. 12, 2017

(30) Foreign Application Priority Data
Feb. 17, 2014 (JP) .................................. 2014-042110

(51) Int. Cl.
*A61K 8/04* (2006.01)
*A61K 8/365* (2006.01)
*A61K 8/34* (2006.01)
*A61K 8/73* (2006.01)
*A61K 8/81* (2006.01)
*A61Q 19/00* (2006.01)
*A61K 8/02* (2006.01)
*A61K 8/85* (2006.01)

(52) U.S. Cl.
CPC ............ *A61K 8/042* (2013.01); *A61K 8/0216* (2013.01); *A61K 8/345* (2013.01); *A61K 8/365* (2013.01); *A61K 8/73* (2013.01); *A61K 8/731* (2013.01); *A61K 8/733* (2013.01); *A61K 8/735* (2013.01); *A61K 8/8147* (2013.01); *A61K 8/85* (2013.01); *A61Q 19/00* (2013.01); *A61K 2800/10* (2013.01); *A61K 2800/242* (2013.01)

(58) Field of Classification Search
CPC .......... A61K 8/365; A61K 8/73; A61K 8/345; A61K 8/735; A61K 8/8147; A61K 8/0216; A61K 8/85; A61K 8/733; A61K 8/731; A61K 8/85; A61K 8/042; A61K 2800/242; A61K 2800/10; A61Q 19/00
See application file for complete search history.

(56) References Cited

U.S. PATENT DOCUMENTS

| 5,456,745 A | 10/1995 | Roreger et al. |
| 2002/0014178 A1* | 2/2002 | Haught ................. A01N 37/40 106/15.05 |
| 2002/0081321 A1* | 6/2002 | Konno ................. A61K 8/0208 424/401 |
| 2004/0131661 A1 | 7/2004 | Auffret et al. |
| 2007/0122360 A1* | 5/2007 | Oniki ..................... A61K 8/042 424/53 |
| 2007/0196441 A1 | 8/2007 | Auffret et al. |
| 2010/0239621 A1 | 9/2010 | Tsujihata |
| 2013/0296761 A1* | 11/2013 | Goto .................... A61K 9/0014 602/54 |
| 2015/0272850 A1 | 10/2015 | Yoneto et al. |
| 2016/0081906 A1 | 3/2016 | Yoneto |

FOREIGN PATENT DOCUMENTS

| EP | 2 210 583 A1 * | 7/2010 |
| JP | 3-81213 A | 4/1991 |
| JP | 6-65048 A | 3/1994 |
| JP | 11-228340 A | 8/1999 |
| JP | 2003-518008 A | 6/2003 |
| JP | 2005-97217 A | 4/2005 |
| JP | 2005-145895 A | 6/2005 |

(Continued)

OTHER PUBLICATIONS

Written Opinion of the International Searching Authority (PCT/ISA/237) for Application No. PCT/JP2015/053761 dated May 12, 2015 (English Translation mailed Sep. 1, 2016.
Supplementary European Search Report for the Application No. EP 15 74 9387 dated Jul. 14, 2017.
International Search Report for the Application No. PCT/JP2015/053761 dated May 12, 2015.
Written Opinion of the International Searching Authority (PCT/ISA/237) for Application No. PCT/JP2015/053761 dated May 12, 2015.
European Office Action for the Application No. 15 749 387.5 dated Jul. 29, 2019.

(Continued)

*Primary Examiner* — Blessing M Fubara
(74) *Attorney, Agent, or Firm* — Cheng Law Group, PLLC

(57) ABSTRACT

A cosmetic gel sheet suitable for a cosmetic field or a medical field is provided.
The cosmetic gel sheet of the present invention contains carboxy group-containing water-soluble polymer, polyalcohol, and acid as essential constituent components. Carboxy group-containing polysaccharide can be suitably used as the carboxy group-containing water-soluble polymer. Water content in the gel sheet is 30% by weight, but it is more preferable if the water content is 10% by weight or less. In the cosmetic gel sheet of the present invention, the gel sheet can be manufactured by drying an aqueous solution containing carboxy group-containing water-soluble polymer, polyalcohol, and acid as essential components. Wherein, it is desirable that content of the acid in the aqueous solution is adjusted to a value appropriate for setting pH of the aqueous solution to 2.0-4.0.

15 Claims, No Drawings

(56) References Cited

FOREIGN PATENT DOCUMENTS

| | | |
|---|---|---|
| JP | 2005-213176 A | 8/2005 |
| JP | 2006-503003 A | 1/2006 |
| JP | 2008-137970 A | 6/2008 |
| JP | 2008-150311 A | 7/2008 |
| JP | 2009-91342 A | 4/2009 |
| JP | 2009-108005 A | 5/2009 |
| JP | 2009-108006 A | 5/2009 |
| JP | 2009-108007 A | 5/2009 |
| JP | 2009-108008 A | 5/2009 |
| JP | 2010-189386 A | 9/2010 |
| JP | 2011-102257 A | 5/2011 |
| JP | 2014-24828 A | 2/2014 |
| WO | WO-01/01950 A1 | 1/2001 |
| WO | WO-2005/063182 A1 | 7/2005 |
| WO | WO-2009/038030 A1 | 3/2009 |
| WO | WO-2015/002091 A1 | 1/2015 |

OTHER PUBLICATIONS

Notification of Reasons for Refusal for the Application No. 2018-205184 from Japan Patent Office dated Oct. 25, 2019.
Notification of Reasons for Refusal for the Application No. 2018-205184 from Japan Patent Office dated Jul. 31, 2020.

* cited by examiner

COSMETIC GEL SHEET AND MANUFACTURING METHOD THEREOF

TECHNICAL FIELD

The present invention relates to new cosmetics using water-soluble polymer gel and a manufacturing method thereof.

BACKGROUND ART

A cosmetic gel sheet is a skin care material, which can give a moist effect, a cold-feeling, and a warm-feeling when attached to skin. The gel sheet can exhibit the effects on the skin for a long period of time without flowing like skin lotion and milky lotion.

A conventional cosmetic gel sheet, gelled by dissolving hydrophilic resin into water, has been used by making water, a moisturizer, and an electrolyte hold in the sheet. The conventional gel sheet contains a large amount of water, and it is essential to crosslink the hydrophilic resin by a crosslinking agent.

A sheet-like pack agent containing collagen and polysaccharide such as chitin, chitosan, alginic acid, and cellulose as constituent components (Patent Document 1), and a skin care cosmetic gel sheet containing polyacrylic acid, polyalcohol, water, and an external crosslinking agent as essential components, and further blended with a keratin softener or a cell-activating ingredient at need (Patent Document 2) are known.

A polysaccharide gel sheet containing red seaweed polysaccharide (such as agar and agarose) and fermentation polysaccharide (such as glucomannan and galactomannan) has been reported (Patent Document 3). Furthermore, a gel sheet consisting of hydrophilic polymer with ionic group and water has been reported (Patent Document 4). As the hydrophilic polymer with ionic group, polyvinyl alcohol derivative, (meth)acrylic ester copolymer, cellulose derivative, and polysaccharide derivative (such as xanthan gum and guar gum) are exemplified.

Two component-based sheet-like pack cosmetics prepared by impregnating a water-insoluble gel sheet of amylose with beauty liquid have been reported (Patent Document 5).

A biomedical adhesive gel sheet using natural polymer with hydrophilic group, such as neutral polysaccharide (cellulose, amylose, amylopectin, dextran, pullulan, inulin, galactan, mannan, xylan, arabinan, glucomannan, galactomannan, hydroxyethyl cellulose, methyl cellulose, etc.), anionic polysaccharide (pectic acid, alginic acid, agarose, agar, carrageenan, fucoidan, hyaluronic acid, chondroitin-sulfuric acid, heparin, gellan gum, native gellan gum, xanthan gum, carboxymethyl cellulose, etc.), cationic polysaccharide (chitin, chitosan, cationized cellulose, etc.), and protein (gelatin, casein, elastin, etc.) has been reported (Patent Document 6).

As a gel sheet containing polysaccharide, a gel sheet containing collagen and a gelling agent and a polyalcohol compound has been also reported (Patent Documents 7 to 9).

It has been indicated that polysaccharide is suitably mixed in a gel sheet (Patent Documents 10 and 11). As the preferable polysaccharide, neutral polysaccharide (e.g. cellulose, amylose, amylopectin, dextran, pullulan, inulin, galactan, mannan, xylan, arabinan, glucomannan, galactomannan, agarose, methyl cellulose, hydroxypropyl cellulose, curdlan, xyloglucan, etc.), anionic polysaccharide (pectic acid, alginic acid, agarose, agar, carrageenan, fucoidan, hyaluronic acid, chondroitin-sulfuric acid, heparin, gellan gum, native gellan gum, xanthan gum, carboxymethyl cellulose, carboxymethyl starch, carboxymethyl dextran, etc.), and cationic polysaccharide (chitin, chitosan, cationized cellulose, cationized starch, cationized dextran, etc.) are exemplified. As the anionic polysaccharide, polysaccharide with carboxy group, sulfo group, or phospho group is shown.

However, these conventional gel sheets are characterized by containing a large amount of water.

PRIOR ART DOCUMENTS

Patent Documents

[Patent Document 1] JP 03-081213 A
[Patent Document 2] JP 11-228340 A
[Patent Document 3] JP 2003-518008 W
[Patent Document 4] JP 2005-145895 A
[Patent Document 5] JP 2005-213176 A
[Patent Document 6] JP 2008-137970 A
[Patent Document 7] JP 2009-091342 A
[Patent Document 8] JP 2009-108005 A
[Patent Document 9] JP 2009-108006 A
[Patent Document 10] JP 2009-108007 A
[Patent Document 11] JP 2009-108008 A

SUMMARY OF INVENTION

Technical Problem

The published gel sheets containing a large amount of water have a problem that, due to heavy weight of the sheet, the sheet slips down if a user does not lie calmly with his or her face upward while the sheet is attached to his or her skin. Furthermore, in winter, coldness of the sheet causes discomfort to a user. The problem to be solved by the present invention is to provide a cosmetic gel sheet which can solve the conventional problems and further give a comfortable warm-feeling when attached to skin.

Solution to Problem

The cosmetic gel sheet according to the present invention made for solving the above-mentioned problems is characterized in that the sheet contains carboxy group-containing water-soluble polymer, polyalcohol, and acid as essential constituent components, and in that water content is 30% by weight or less.

As used herein, the carboxy group-containing water-soluble polymer refers to water-soluble polymer having carboxy group as a substituent in the molecule.

The water content in the cosmetic gel sheet is more preferably 15% by weight or less.

The cosmetic gel sheet according to the present invention is characterized in that the water content in the sheet is extremely low in comparison to the conventional cosmetic sheet, so there is no problem if the water content is substantially zero.

If the water content in the cosmetic gel sheet is 30% by weight or more, the water-soluble polymer is insufficiently gelled, so the gel sheet is inappropriate as a cosmetic sheet due to its insufficient mechanical strength. Namely, although the cosmetic gel sheet according to the present invention is convenient for manufacture with water in a raw material preparation phase, it is characterized in that the water is not necessary in a product. The cosmetic gel sheet is preferably manufactured by evaporating and volatilizing the water and reducing the water content in the gel sheet in the manufacturing process.

The low water content in the gel sheet, which does not have any physical problem, causes an increased energy cost for the evaporation of the water. Therefore, the water may be practically remained to an extent that a property of the cosmetic gel sheet is not damaged.

Although the carboxy group-containing water-soluble polymer includes carboxy group-containing synthetic polymer, such as polyacrylic acid and copolymer thereof, and carboxy group-containing polysaccharide, the latter is more preferable in the present invention. This is because, in the carboxy group-containing water-soluble synthetic polymer, residual monomer with a malodor is concerned.

Since the cosmetic gel sheet can be handled by itself, a support is not required. However, there is no problem if the support is added.

When an aqueous solution containing the carboxy group-containing water-soluble polymer, the acid, and the polyalcohol is prepared and then the water is evaporated to lower pH, the water-soluble polymer is pseudo-crosslinked by mutual association of the carboxy group and easily gelled. The cosmetic gel sheet according to the present invention utilizes this property of the carboxy group-containing water-soluble polymer.

The cosmetic gel sheet is not required to contain water-soluble divalent ions. In the case of the conventional hydrogel sheet containing a large amount of water (in a proportion of 70% by weight or more based on the gel sheet), for gelling the carboxy group-containing water-soluble polymer, crosslink by water-soluble divalent metal ions is required (Patent Documents 1 and 2). According to the present invention, since the mutual association of the carboxy group by reducing the water content in the gel is utilized, the metal salt is not required.

Furthermore, in the gel sheet with a large amount of water and the mutual association by the divalent metal ions, even if skin is massaged with water after the gel sheet is applied, the carboxy group-containing polysaccharide cannot be dissolved into the water. A mechanism of the gel association is distinctively different between the conventional hydrogel sheet and the cosmetic gel sheet according to the present invention.

A preferable content of each component in the cosmetic gel sheet is as follows.

The polyalcohol is preferably from 10 parts by weight to 1,000 parts by weight based on 1 part by weight of the water-soluble polymer.

The content of the acid is adjusted so that pH of the raw material aqueous solution becomes appropriate for the association of the carboxy group-containing water-soluble polymer. For example, when 120 parts by weight of water are used based on 1 part by weight of the carboxy group-containing water-soluble polymer, the content of the acid is preferably adjusted to a value required for setting pH of the aqueous solution to 4.5-2.0. If the content of the water is lower, pH may be set to a lower value depending on the low content, whereas, if the content of the water is larger, pH may be set to a larger value depending on the large content. In the case of the exemplified water content, if pH is 4.5 or more, gel with sufficient strength cannot be obtained when the water is dried. Whereas, pH of 2.0 or less is not preferable since the raw material aqueous solution is easily gelled before the water is dried, and further, even if the gel sheet can be generated by drying the water, the gel sheet gives stimulus to a face when attached.

Although the carboxy group-containing water-soluble polymer is gelled by the mutual association of the carboxy group under acidic condition, if pH approaches neutral, gel structure is broken and becomes water-soluble. Namely, the gel structure is reversibly in the gel state or in the soluble state according to pH change. Therefore, when the sheet is attached to skin in the gel state and then the skin is massaged with an appropriate amount of water, polysaccharide gel is solubilized, so the polysaccharide and a blended valuable component can be effectively absorbed into the skin.

In an acid concentration at which pH of the aqueous solution is 2.0 or less, since the gel structure is strong, the structure hardly becomes the soluble state even if the appropriate amount of water is added to massage. As used herein, the appropriate amount refers to an amount so as not to flow down from a face when the cosmetic gel sheet is attached to the face and then water is added. It is practically meaningless that water is added in an amount so as not to be remained on a face.

The polyalcohol has a property for generating heat when brought into contact with water. The polyalcohol as a maximum component in the gel sheet generates heat when the gel sheet is attached to skin and then water is added, so a comfortable warm-feeling is given to the skin. The conventional gel sheet does not significantly generate heat due to its large water content, whereas the gel sheet according the present invention with low water content can give the warm-feeling.

As the carboxy group-containing polysaccharide, xanthan gum, gellan gum, alginic acid, carboxymethyl cellulose, hyaluronic acid with carboxy group, and the like are preferably used. They may be metal salt such as sodium salt or potassium salt.

Molecular weight of the carboxy group-containing water-soluble polymer is preferably within a range from approximately $5*10^4$ to $5*10^6$ Dalton. Different water-soluble polymer, or the same water-soluble polymer with different molecular weight may be mixed for use so long as the molecular weight is within this range. Also, water-soluble polymer within this molecular weight range and water-soluble polymer with lower molecular weight than this range can be mixed for use.

The content of the carboxy group-containing water-soluble polymer is preferably within a range from 0.1% by weight to 10% by weight based on the whole gel. If the content of the carboxy group-containing water-soluble polymer is less than 0.1% by weight, the gel is softened, so gel with an excellent elastic body cannot be formed. Whereas, if the content is more than 10% by weight, the gel is hardened, so the gel with the excellent elastic body cannot be formed and further adhesiveness to skin is poor.

As the acid used in the present invention, monobasic acid such as hydrochloric acid, acetic acid, and lactic acid, polybasic acid such as citric acid, oxalic acid, and tartaric acid, and the like can be used. Citric acid, tartaric acid, and lactic acid are particularly preferable. Furthermore, two or more kinds of the acid can be mixed for use.

The polyalcohol used in the present invention is not particularly limited, but glycerin, propylene glycol, ethylene glycol, polyethylene glycol, 1,3-butylene glycol, dipropylene glycol, sorbitol, and the like can be used. Among them, glycerin is particularly preferable.

The content of the polyalcohol is preferably within a range from 10 to 1,000 or more parts by weight, more preferably within a range from 30 to 500 parts by weight, based on 1 part by weight of the carboxy group-containing water-soluble polymer. If the content of the polyalcohol is less than 10 parts by weight, the sheet becomes hard gel rather than the gel with the excellent elastic body having appropriate skin attachability. Whereas, if the content is more than 1,000 parts by weight, the gel is softened or the gel formation becomes impossible.

In the carboxy group-containing polysaccharide gel, the water as an original maximum component among the blending raw materials is volatilized in drying process, so the polyalcohol becomes the maximum component.

The gel sheet according to the present invention is gelled by the mutual association of the carboxy group-containing polymer, and has mechanical strength. Furthermore, when pH is increased, the gel structure is decayed and dissolved. This type of the gel sheet is firstly put into practical use by the present invention. When strength of the gel sheet according to the present invention was measured with a tensile testing machine, rupture stress was $0.05N/cm^2$ or more. If the rupture stress is $0.05N/cm^2$ or less, structure of the gel sheet itself is hardly kept, so the seat is difficult to be formed.

In the cosmetic gel sheet, the valuable component such as cosmetic and pharmaceutical components can be blended within a range which does not affect the object and an effect of the present invention. Particularly, it is advantageous for application as cosmetics and a quasi-drug. The blendable component includes, for example, whitening component, anti-wrinkle component, anti-inflammatory component, blood circulation promoting component, anti-microbial component, anti-pruritic component, various vitamins and derivatives thereof, anti-oxidative component, pigment, fragrance, and the like. The cosmetic and pharmaceutical components to be blended can be added to the raw material aqueous solution.

The whitening component is not particularly limited, but, for example, vitamin C derivative such as ascorbic acid phosphoric ester magnesium salt, ascorbic acid glucoside and salts and acyl derivative thereof, ethylascorbic acid, and ascorbyl palmitate, α-arbutin, β-arbutin, kojic acid, placenta extract, cysteine, glutathione, ellagic acid, rucinol, tranexamic acid, baicalein, adenosine and phosphoric acid sodium salt thereof, astaxanthin, deer horn shaped *Ganoderma lucidum*, oil-soluble licorice, lavender, lempuyang, burnet, resveratrol, *Ganoderma lucidum*, extracts and tincture thereof, or components contained therein, and the like are included.

The anti-wrinkle component is not particularly limited, but, for example, retinoid such as retinol, retinoic acid, retinol acetate, and retinol palmitate, α-hydroxy acid such as citric acid, fruit acid, glycolic acid, and lactic acid, α-hydroxyl acid cholesterol, rutin derivative, N-methylserine, elastin, collagen, sericin, centella asiatica extract, scutellaria baicalensis extract, and the like are included.

The anti-inflammatory component is not particularly limited, but, for example, glycyrrhetinic acid, ghycyrrhetinic acid 2K, allantoin, epsilon-aminocaproic acid, azulene, shikonin, tranexamic acid, and *Coptis japonica*, licorice, Terminalia, yarrow, lithospermum root, comfrey, aloe, butcher's bloom, horse chestnut, peach leaf, loquat leaf, and extracts and tincture thereof, or components contained therein, and the like are included.

The blood circulation promoting component is not particularly limited, but, for example, vitamin E, nicotinic acid, nicotinic acid amide, benzyl nicotinate, nicomol, caffeine, capsaicin, nonanoic acid vanillylamide, shogaol, gingerol, and the like are included.

The anti-microbial component is not particularly limited, but, for example, cationic surfactant such as isopropyl methylphenol, triclosan, triclocarban, trichloro-hydroxyphenol, halocarbon, benzalkonium chloride, and benzethonium chloride, photosensitizer, zinc oxide, titanium oxide, chitin, chitosan, hinokiol, anise, and the like are included.

The anti-pruritic component is not particularly limited, but, for example, diphenhydramine hydrochloride, chlorpheniramine maleate, crotamiton, glycyrrhizin acid, menthol, camphor, rosemary oil, capsaicin, nonanoic acid vanillylamide, dibucaine, and the like are included.

The vitamins are not particularly limited, but, for example, as oil-soluble vitamins, vitamin A oil, cod-liver oil, retinol acetate, retinol palmitate, retinol, dehydroretinol, vitamin $A_3$, retinoic acid, vitamin D, vitamin $D_2$ (ergocalciferol), vitamin $D_3$ (cholecalciferol), vitamin derivative, vitamin E (tocopherol), dl-α-tocopherol acetate, dl-α-tocopherol, tocopherol butyrate, tocopheryl nicotinate, nicotinic acid benzyl ester, natural vitamin E, vitamin K, vitamin U, and the like are included. Also, as water-soluble vitamins, vitamin $B_1$ (thiamin), vitamin $B_2$ (riboflavin tetrabutyrate), vitamin $B_6$ (fatty acid ester such as pyridoxine dicaprylate and pyridoxine dipalmitate), vitamin $B_{12}$ (cobalamin), vitamin $B_{13}$, vitamin $B_{14}$, vitamin $B_{15}$ (pangamic acid), folic acid, carnitine, thioctic acid, pantothenyl alcohol, pantothenyl ethyl ether, pantothenic acid, nicotinic acid, nicotinic-acid amide, choline, inositol, vitamin C (ascorbic acid), ascorbyl stearate, ascorbyl pantothenate, ascorbyl dipalmitate, vitamin H (biotin), vitamin P (hesperidin), Apprecier, and the like are included.

The anti-oxidative component is not particularly limited, but, for example, polyphenols such as anthocyanin, catechin, green tea polyphenol, and apple polyphenol, carotenoid such as ascorbic acid, sodium ascorbate, sodium sulfate ascorbate, β-carotene, and astaxanthin, β-diketone such as tocopherols, tocopherol acetate, natural vitamin E, tocomonoenol, tocotrienol, and curcumin, lignin such as sesamin and sesamolin, phenol such as eugenol, and the like are included.

Anti-allergic component is not particularly limited, but, for example, glycyrrhetinic acid derivative such as glycyrrhetinic acid and glycyrrhetinic acid 2K, licorice, chlorella, comfrey, moutan cortex, *Tilia cordata, Isodon japonicus*, sage, shiso, mugwort, extracts and tincture thereof or components contained therein, and the like are included.

The cosmetic gel sheet according to the present invention can be manufactured by uniformly dissolving the carboxy group-containing water-soluble polymer, the acid, and the polyalcohol into water and then suitably drying and transpiring the water to be brought into intended form.

Specifically, an aqueous solution containing the carboxy group-containing water-soluble polymer, the polyalcohol, and the acid is mixed for preparation with a propeller type rotary stirrer. The prepared aqueous solution is applied on a polyethylene terephthalate film in a uniform thickness, then it is dried with hot air, and thereby a transparent gel sheet with the uniform thickness can be manufactured. It should be noted that the film is preferably dried so that water content becomes 30% by weight or less. The gel sheet is cut into circle, oval, comma shape, or face shape to obtain a product as sheet-like cosmetics.

Also, the prepared aqueous solution may be poured into a tray and then dried to evaporate the water. When the tray is formed in comma shape, face shape, or the like, the cutting of the seat is not required.

A material of the tray is preferably a material impervious to oxygen and steam or a composite of the materials, which is preferably made of plastic with a frame member. The tray made of plastic can be fabricated by heat molding or thin wall injection molding. The frame member is fabricated using thermoplastic such as polypropylene or polyethylene terephthalate or a composite of the thermoplastic such as polyethylene terephthalate/aluminum/polyethylene.

When the cosmetic gel sheet is applied to a face, the polyalcohol generates heat by absorbing steam or water on a surface of the face to give a warm-feeling on the face.

When the appropriate amount of water is added to massage the face after the application of the cosmetic gel sheet, the gel sheet is gradually dissolved while giving a warm-feeling on the face. This is because a pH value rises in accordance with an increase in the water content.

Advantageous Effects of Invention

In the cosmetic gel sheet according to the present invention, water is not an essential component and the carboxy group-containing water-soluble polymer is gelled in the polyalcohol. This type of the cosmetic gel sheet has the following characteristics.

(1) Since the low water content is not suitable for propagation of microorganism, an antiseptic agent is not required.

(2) A main component is the polyalcohol, so the alcohol generates heat by hydration to give a comfortable feeling to skin when the skin is massaged with water (hot water) after application of the gel sheet.

(3) Stability of a cosmetic valuable component unstable to water is increased.

The cosmetic gel sheet according to the present invention utilizes an excellent original property of the water-soluble polymer and the polysaccharide. The carboxy group-containing water-soluble polymer gel which is not chemically crosslinked gives a warm-feeling by the hydration of the polyalcohol when a small amount of water is added after application to skin, and, when the skin is massaged, the gel is dissolved, so the blended component is penetrated into the skin. Then, even when the gel is washed away with water, the effects are sustained to give the warm-feeling, a moisture feeling, and a smooth feeling to the skin. Therefore, the gel is useful as a material to be used in a cosmetic field. These effects have not been observed in the conventional hydrogel sheet.

DESCRIPTION OF EMBODIMENTS

Hereinafter, the present invention will be described with reference to Examples, but the present invention is not of course limited to the following Examples.

Manufacture of the Polysaccharide Gel Sheet

Aqueous solutions containing carboxy group-containing water-soluble polymer, polyalcohol, and acid were stirred and mixed according to blending ratios (part by weight) described in the following Table 1 with a propeller type rotary stirrer to prepare raw material aqueous solutions. Tocopherol and Apprecier were dissolved into a small amount of ethanol and then added. The prepared raw material aqueous solutions were applied on polyethylene terephthalate films with a uniform thickness of 25 µm and then dried at 60 to 80° C. for 5 to 30 minutes with a gear type oven to obtain a cosmetic gel sheet with a thickness of approximately 200 µm or a non-gelled viscous material. The water content in the gel was adjusted by changing drying temperature and drying time.

Only pH of the raw material aqueous solutions which were measured are shown in a right-end column of Table 1.

Standards and sources of each raw material are as follows. ARONVIS AH-106X (TOAGOSEI CO., LTD.) was used as polyacrylic acid, while hyaluronic acid with molecular weight of about 800,000 (FCH-80, Kikkoman Biochemifa Company) was used as hyaluronic acid (H80) in Examples 5 and 9, and hyaluronic acid with molecular weight of about 2,000,000 (FCH-200, Kikkoman Biochemifa Company) was used as hyaluronic acid (H200) in Examples 13, 14, and 15. As the other raw materials, glycerin (concentrated glycerin, MIYOSHI OIL & FAT CO., LTD.), citric acid (NACALAI TESQUE, INC.), trisodium ascorbyl palmitate phosphate (Apprecier, SHOWA DENKO K.K.), tocopherol (NACALAI TESQUE, INC.), xanthan gum (SANSHO Co., Ltd.), gellan gum (Wako Pure Chemical Industries, Ltd.), CMC1260 as carboxymethyl cellulose (DAICEL FINECHEM LTD.), and alginic acid (Kikkoman Biochemifa Company) were used. Lactic acid, ethylene glycol, hydrochloric acid, and acetic acid of guaranteed reagent (NACALAI TESQUE, INC.) were used.

The amounts of the hydrochloric acid and the acetic acid are shown in converted parts by weight from the aqueous solution reagent.

Comparison of Properties among the Manufactured Polysaccharide Gel Sheets

Evaluation results of the polysaccharide gel sheets in Examples 1 to 15 and Comparative Examples 1 and 2 are shown in the following Table 2. Contents of the respective evaluation results are as follows.

1. Results of Properties Observation

Observation results of flexibility, elasticity, and tensile strength by naked eyes and touch are shown.

2. Results of Water Content Measurement

Measurement results of water content in the gel are shown. The water content measurements were determined from weight reduction values before and after heating samples at 90° C. for 1 hour.

3. Results of Test on Adhesiveness to Skin

Test results on adherence to skin when the polysaccharide gel sheets (2 cm*2 cm) were applied inside a forearm of a human volunteer are shown.

4. Results of Test on Warm-feeling

Test results on a warm-feeling to skin when the polysaccharide gel sheets (2 cm*2 cm) were applied inside a forearm of a human volunteer are shown.

5. Test on Solubility

The polysaccharide gel sheets (2 cm*2 cm) were applied on a forearm of a human volunteer, on which 1 ml of water was dripped and then the skin was massaged over the sheets for 3 minutes to observe solubility of the gel.

6. Test on Mechanical Strength

The polysaccharide gel sheets were punched in a dumbbell shape with a width of 1.5 cm, and then a tensile test was performed at a tensile speed of 1 cm/min with both ends supported to measure rupture strength. A unit of the numeric values is N/cm². A compact table-top tester EZ Test EZ-SX manufactured by SHIMADZU CORPORATION was used.

For the properties in Table 2, A represents that all of the flexibility, the elasticity, and the tensile strength are sufficient, B represents that the flexibility and the elasticity are sufficient, C represents that the flexibility and the elasticity are insufficient, and D represents that the manufactured product was liquid.

For the test on adhesiveness to skin in Table 2, A represents good adhesiveness, B represents adhesiveness with partial detachment, and C represents no adhesiveness and completely detached. In the case of the products evaluated as C or D in the observation results of the properties, a practical seat was not formed, so the test was not possible.

For the test on warm-feeling in Table 2, A represents excellent warm-feeling to the skin, B represents sufficient warm-feeling, and C represents no warm-feeling. To the products which could not be formed in a sheet shape, the test was not possible.

For the test on solubility in Table 2, A represents completely dissolved, and B represents partially dissolved. To the products which could not be formed in a sheet shape, the test was not possible.

Face Mask: Example 16

1 part by weight of alginic acid, 80 parts by weight of glycerin, 0.5 parts by weight of tartaric acid, 0.05 parts by weight of tocopherol, and 0.05 parts by weight of vitamin C derivative were added to 120 parts by weight of water, and then mixed well to obtain a homogeneous solution. The solution was poured into a human face shaped tray made by heat-molding polypropylene to a depth of 3 mm from a bottom of the tray. After pouring, the water was evaporated by hot air drying at 75° C. for 2 hours to form a gel sheet. The gel sheet was removed from the tray and cut into a shape of a face seat to perform the respective evaluations to a face. Adhesiveness to skin, heating property, and water-solubility were all good.

TABLE 1

| | constituent component | | | | | | | |
|---|---|---|---|---|---|---|---|---|
| | carboxy group-containing water-soluble polymer | | | | | | polyalcohol | |
| | xanthan gum | gellan gum | alginic acid | hyaluronic acid | carboxymethyl cellulose | polyacrylic acid | glycerin | ethylene glycol |
| Examples | | | | | | | | |
| 1 | 1 | | | | | | 80 | |
| 2 | | 1 | | | | | 60 | |
| 3 | | | 1 | | | | 50 | |
| 4 | | | 1 | | | | 10 | |
| 5 | | | | 1 | | | 50 | |
| 6 | 1 | | | | | | 100 | |
| 7 | | 1 | | | | | 80 | |
| 8 | | | 1 | | | | | 90 |
| 9 | | | | 1 | | | | 90 |
| 10 | | | | | 1 | | 80 | |
| 11 | | | | | 1 | | | 100 |
| 12 | | | | | | 1 | 50 | |
| 13 | | | | 1 | | | 900 | |
| 14 | | | | 1 | | | 500 | |
| 15 | | | | 1 | | | 200 | |
| Comparative Examples | | | | | | | | |
| 1 | 1 | | | | | | 80 | |
| 2 | | 1 | | | | | 60 | |

| | constituent component | | | | | | |
|---|---|---|---|---|---|---|---|
| | acid | | | valuable component | | | raw material aqueous solution |
| | citric acid | lactic acid | hydrochloric acid | tocopherol | Appreciér | water | pH |
| Examples | | | | | | | |
| 1 | | | 0.5 | | | 120 | |
| 2 | | 0.9 | | 0.05 | | 120 | 3.5 |
| 3 | 0.6 | | | | | 120 | |
| 4 | 0.6 | | | | | 90 | 3.5 |
| 5 | 0.5 | | | | 0.05 | 100 | |
| 6 | | 0.6 | | | | 120 | |
| 7 | 0.6 | | | | | 120 | 3.5 |
| 8 | | | 0.5 | 0.1 | | 120 | |
| 9 | | 0.9 | | 0.1 | | 120 | |
| 10 | 0.6 | | | | | 120 | 3.0 |
| 11 | | 0.9 | | 0.05 | | 120 | 3.5 |
| 12 | 0.6 | | | 0.05 | | 120 | |
| 13 | 1.5 | | | | | 120 | |

TABLE 1-continued

| | | | | | |
|---|---|---|---|---|---|
| 14 | 0.9 | | 0.4 | 120 | |
| 15 | | 0.5 | 0.4 | 120 | |
| Comparative Examples | | | | | |
| 1 | | 0.5 | | 120 | |
| 2 | 0.9 | | 0.05 | 120 | 3.5 |

TABLE 2

| | | property | water weight | test on adhesiveness to skin | test on warm-feeling | test on solubility | test on mechanical strength |
|---|---|---|---|---|---|---|---|
| Examples | 1 | A | 9.5 | A | A | A | 0.4 |
| | 2 | A | 9.4 | A | A | A | |
| | 3 | A | 9.5 | A | A | A | |
| | 4 | A | 8.5 | A | A | A | 2.4 |
| | 5 | A | 9.0 | A | A | A | |
| | 6 | A | 9.3 | A | A | A | 0.9 |
| | 7 | A | 9.5 | A | A | A | |
| | 8 | A | 15.2 | A | A | A | |
| | 9 | A | 20.5 | A | B | A | 0.6 |
| | 10 | A | 7.5 | A | A | A | |
| | 11 | A | 8.0 | A | A | A | |
| | 12 | A | 9.2 | A | A | A | |
| | 13 | A | 11.3 | A | A | A | 0.06 |
| | 14 | A | 9.4 | A | A | A | 0.1 |
| | 15 | A | 25.4 | A | B | A | |
| Comparative Examples | 1 | D | 44.5 | unperformable | not performed | not performed | |
| | 2 | D | 34.5 | unperformable | not performed | not performed | |

The invention claimed is:

1. A cosmetic gel sheet, wherein the cosmetic gel sheet consists essentially of a carboxy group-containing water-soluble polymer, polyalcohol, acid, water, and optionally, a valuable component, and water content is 9.0% by weight or less,
wherein the cosmetic gel sheet has a rupture stress of 0.05 N/cm$^2$ or more,
wherein a content of the polyalcohol is from 10 parts by weight to 1,000 parts by weight based on 1 part by weight of the carboxy group-containing water-soluble polymer, and
wherein the valuable component is selected from the group consisting of whitening components, anti-wrinkle components, anti-inflammatory components, blood circulation promoting components, anti-microbial components, anti-pruritic components, vitamins and derivatives thereof, anti-oxidative components, anti-allergic components, pigments, and fragrances.

2. The cosmetic gel sheet according to claim 1, characterized in that the carboxy group-containing water-soluble polymer is carboxy group-containing polysaccharide.

3. The cosmetic gel sheet according to claim 2, characterized in that the carboxy group-containing polysaccharide is one or more compound selected from a group consisting of xanthan gum, gellan gum, alginic acid, hyaluronic acid, and carboxymethyl cellulose.

4. The cosmetic gel sheet according to claim 1, characterized in that, when an aqueous solution containing the carboxy group-containing water-soluble polymer, the polyalcohol, and the acid as essential components is dried to manufacture the gel sheet, content of the acid is appropriate for setting pH of the aqueous solution to 2.0-4.5.

5. The cosmetic gel sheet according to claim 1, characterized in that the cosmetic gel sheet generates heat when attached to skin.

6. The cosmetic gel sheet according to claim 1, characterized in that the polyalcohol is glycerin.

7. The cosmetic gel sheet according to claim 1, characterized, in that the acid is one or more compound selected from a group consisting of citric acid, tartaric acid, lactic acid, and hydrochloric acid.

8. The cosmetic gel sheet according to claim 1, characterized in that the cosmetic gel sheet has a support.

9. The cosmetic gel sheet according to claim 1, wherein the water content is 8.5% by weight or less.

10. The cosmetic gel sheet according to claim 1, wherein the water content is 8.0% by weight or less.

11. The cosmetic gel sheet according to claim 1, wherein the valuable component is an anti-allergic component comprising at least one selected from the group consisting of glycyrrhetinic acid derivatives, licorice chlorella, comfrey, moutan cortex, *Tilia cordata, Isodon japonicus*, sage, shiso, and mugwort.

12. The cosmetic gel sheet according to claim 1, wherein the cosmetic gel sheet consists of the carboxy group-containing water-soluble polymer, polyalcohol, acid, water, and optionally, the valuable component.

13. The cosmetic gel sheet according to claim 12, wherein the valuable component is an anti-pruritic component selected from the group consisting of crotamiton, glycyrrhizin acid, rosemary oil, and dibucaine.

14. The cosmetic gel sheet according to claim 12, wherein the valuable component is a blood circulation promoting component selected from the group consisting of nicomol, caffeine, shogaol, and gingerol.

15. A method of manufacturing the cosmetic gel sheet according to claim 1, comprising applying an aqueous solution containing the carboxy group-containing water-soluble polymer, polyalcohol, acid and optionally, valuable component on a film or pouring said aqueous solution into a tray, and then drying said aqueous solution such that water content is 9% by weight or less in order to manufacture the cosmetic gel sheet.

* * * * *